(12) United States Patent
Chen et al.

(10) Patent No.: US 9,828,358 B2
(45) Date of Patent: *Nov. 28, 2017

(54) COMPOSITIONS COMPRISING AN INHIBITOR OF LYSINE SPECIFIC DEMETHYLASE-1

(71) Applicant: Celgene Quanticel Research, Inc., San Diego, CA (US)

(72) Inventors: Young K. Chen, San Marcos, CA (US); Toufike Kanouni, La Jolla, CA (US); Stephen W. Kaldor, San Diego, CA (US); Jeffrey Alan Stafford, San Diego, CA (US); James Marvin Veal, Apex, NC (US); Paula Alessandra Tavares-Greco, Parsippany, NJ (US); Matthew Michael Kreilein, Hillsborough, NJ (US)

(73) Assignee: CELGENE QUANTICEL RESEARCH, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/344,426

(22) Filed: Nov. 4, 2016

(65) Prior Publication Data

US 2017/0129871 A1    May 11, 2017

Related U.S. Application Data

(60) Provisional application No. 62/251,507, filed on Nov. 5, 2015.

(51) Int. Cl.
| | | |
|---|---|---|
| *C07D 401/04* | (2006.01) | |
| *A61K 31/506* | (2006.01) | |
| *C07D 239/36* | (2006.01) | |
| *A61K 31/4545* | (2006.01) | |

(52) U.S. Cl.
CPC ........ *C07D 401/04* (2013.01); *A61K 31/4545* (2013.01); *A61K 31/506* (2013.01); *C07D 239/36* (2013.01)

(58) Field of Classification Search
CPC  C07D 239/36; C07D 401/04; A61K 31/4545; A61K 31/506
USPC ........................... 544/319, 320; 514/269, 272
See application file for complete search history.

(56) References Cited

U.S. PATENT DOCUMENTS

| | | |
|---|---|---|
| 9,255,097 B2 | 2/2016 | Chen et al. |
| 9,573,930 B2 * | 2/2017 | Chen ................... C07D 403/12 |
| 2003/0232813 A1 | 12/2003 | Agarwal et al. |
| 2007/0270446 A1 | 11/2007 | Marquis, Jr. et al. |
| 2010/0137313 A1 | 6/2010 | Boriack-Sjodin et al. |
| 2016/0130247 A1 | 5/2016 | Chen et al. |
| 2016/0152595 A1 | 6/2016 | Chen et al. |

OTHER PUBLICATIONS

Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431, 2001.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-1010, 1996.*
Serajuddin, Advanced Drug Delivery Reviews 59 (2007) 603-616.*
Bastin et al., Organic Process Research & Development 2000, 4, 427-435.*
Liu, Rong, ed., Water-Insoluble Drug Formulation (CRC Press, 2008) Chapter 15 pp. 417-435.*
Morris, et al., International Journal of Pharmaceutics 105 (1994) 209-217.*
Adeyeye, Moji, ed., Preformulation in Solid Dosage Form Development (Informa Healthcare, 2008) Chapter 2.3, pp. 63-80.*
Swarbrick et al., eds. Encyclopedia of Pharmaceutical Technology 13 (Marcel Dekker, NY 1996) pp. 453-499.*
Gould, International J. of Therapeutics 33,201 (1986).*
International Search Report and Written Opinion, dated Jan. 9, 2017, by international Bureau o f WIPO in related to International Patent Application No. PCT/US16/60694.

* cited by examiner

*Primary Examiner* — Deepak Rao
(74) *Attorney, Agent, or Firm* — Wiley Rein LLP

(57) ABSTRACT

Described herein are amorphous and crystalline forms of pharmaceutically acceptable salts of the lysine specific demethylase-1 inhibitor 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile. Also described are pharmaceutical compositions suitable for administration to a mammal that include the lysine specific demethylase-1 inhibitor, and methods of using the lysine specific demethylase-1 inhibitor for treating diseases or conditions that are associated with lysine specific demethylase-1 activity.

20 Claims, 3 Drawing Sheets

COMPOSITIONS COMPRISING AN INHIBITOR OF LYSINE SPECIFIC DEMETHYLASE-1

RELATED APPLICATION

This application claims priority benefit of U.S. Provisional Patent Application No. 62/251,507, filed Nov. 5, 2015, incorporated fully herein by reference for all purposes.

FIELD OF THE INVENTION

Described herein is the lysine specific demethylase-1 inhibitor 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, and pharmaceutically acceptable salts, solvates, and crystalline forms thereof.

BACKGROUND OF THE INVENTION

A need exists in the medicinal arts for an effective treatment of cancer and neoplastic disease. Lysine specific demethylase-1 has been implicated in a number of diseases or conditions, such as breast cancer, lung cancer, prostate cancer, glioblastoma, and leukemia, as well as others diseases or conditions.

SUMMARY OF THE INVENTION

Described herein is 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, pharmaceutically acceptable salts, pharmaceutically acceptable solvates (including hydrates), polymorphs, and amorphous phases thereof, and methods of use thereof.

In one aspect, described herein is a pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, wherein the pharmaceutically acceptable salt is in crystalline form. In some embodiments, the pharmaceutically acceptable salt is besylate salt, wherein the pharmaceutically acceptable salt is in crystalline form.

In one aspect, described herein is a crystalline Form 1 of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt that is characterized as having:
- (a) an X-Ray powder diffraction (XRPD) pattern substantially the same as shown in FIG. 1;
- (b) an X-ray powder diffraction (XRPD) pattern with characteristic peaks at 4.9° 2-Theta, 9.7° 2-Theta, 13.4° 2-Theta, 18.0° 2-Theta, 18.5° 2-Theta;
- (c) a DSC thermogram with an endotherm having an onset temperature at about 317° C.;
- (d) a DSC thermogram substantially similar to the one set forth in FIG. 2; or
- (e) combinations thereof.

Also described herein is a pharmaceutical composition comprising a crystalline form of a pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, and at least one additional ingredient selected from pharmaceutically acceptable carriers, diluents and excipients. In some embodiments, the pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile is a besylate salt. In some embodiments, the pharmaceutical composition is in a form suitable for oral administration to a mammal. In some embodiments, the pharmaceutical composition is in an oral solid dosage form. In some embodiments, the pharmaceutical composition comprises about 0.5 mg to about 200 mg of crystalline 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt.

In some embodiments, described herein is a pharmaceutical composition comprising a crystalline form of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt as described herein, and at least one additional ingredient selected from pharmaceutically acceptable carriers, diluents and excipients. In some embodiments, the pharmaceutical composition includes Form 1 of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt. In some embodiments, the pharmaceutical composition is in a form suitable for oral administration to a mammal. In some embodiments, the pharmaceutical composition is in an oral dosage form. In some embodiments, the pharmaceutical composition is in an oral solid dosage form. In some embodiments, the pharmaceutical composition is in the form of a tablet, pill, or capsule. In some embodiments, the pharmaceutical composition is in the form of a capsule. In some embodiments, the pharmaceutical composition is in the form of a tablet. In some embodiments, the pharmaceutical composition is in the form of a moisture barrier coated tablet. In some embodiments, the pharmaceutical composition comprises about 0.5 mg to about 200 mg of crystalline 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt. In some embodiments, the pharmaceutical composition comprises about 0.5 mg to about 200 mg of crystalline 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt.

Also provided is an article of manufacture comprising multiple unit doses of the oral solid dosage form pharmaceutical composition described herein in a high-density polyethylene (HDPE) bottle equipped with a high-density polyethylene (HDPE) cap. In some embodiments, high-density polyethylene (HDPE) bottle further comprises an aluminum foil induction seal and silica gel desiccant.

Also described herein is 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt that is in amorphous form. Also described herein is a pharmaceutical composition comprising amorphous 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt, and at least one additional ingredient selected from pharmaceutically acceptable carriers, diluents and excipients. In some embodiments, the pharmaceutical composition is in a form suitable for oral administration to a mammal. In some embodiments, the pharmaceutical composition is in an oral solid dosage form.

In one aspect, described herein is the use of a crystalline form of a pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile in the treatment of cancer in a mammal. In another aspect, described herein is the use of crystalline 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt in the treatment of cancer in a mammal. In another aspect, described herein is the use of amorphous 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt in the treatment of cancer in a mammal. In some embodiments, the cancer is amenable to treatment with a lysine specific demethylase-1 inhibitor. In some embodiments, the cancer is breast cancer, lung cancer, prostate cancer, glioblastoma, or leukemia.

In certain embodiments described herein, a crystalline form of a pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile is used in the manufacture of a medicament for the treatment or prevention of diseases, disorders, or conditions associated with lysine specific demethylase-1 activity.

Also described is a method of treating cancer in a mammal comprising administering to the mammal a crystalline pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile. In some embodiments, the crystalline pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile is the besylate salt. In some embodiments, the cancer is breast cancer, lung cancer, prostate cancer, glioblastoma, or leukemia.

Also provided is the use of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt for the manufacture of a medicament for the treatment or prevention of cancer in a human. Further provided is the use of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt for the manufacture of a medicament for the treatment or prevention of cancer in a human wherein the cancer is breast cancer, lung cancer, prostate cancer, glioblastoma, or leukemia. In some embodiments, 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt is crystalline.

Also described herein are processes for the preparation of crystalline form of a pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile.

Also described herein are processes for the preparation of crystalline 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt. The disclosed processes provide for the preparation of crystalline 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt in good yield and high purity.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the invention will become apparent to those skilled in the art from this detailed description.

DETAILED DESCRIPTION

Figure 1:
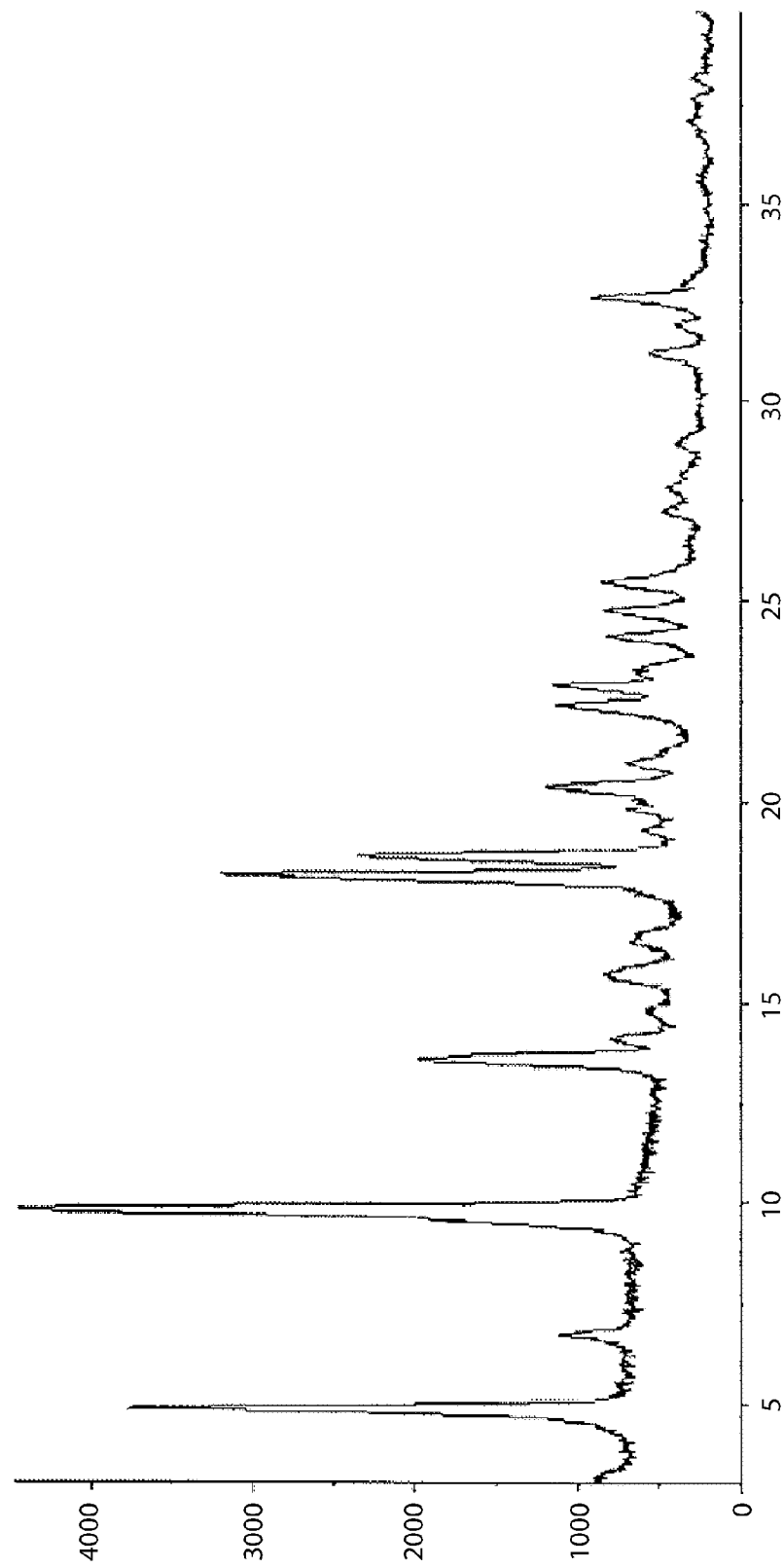
FIG. 1 illustrates the XRPD of Form 1 of crystalline 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt.

Epigenetics is the study of heritable changes in gene expression caused by mechanisms other than the underlying DNA sequence. Molecular mechanisms that play a role in epigenetic regulation include DNA methylation and chromatin/histone modifications.

The genomes of eukaryotic organisms are highly organized within the nucleus of the cell. Tremendous compaction is required to package the 3 billion nucleotides of the human genome into the nucleus of a cell. Chromatin is the complex of DNA and protein that makes up chromosomes. Histones are the major protein component of chromatin, acting as spools around which DNA winds. Changes in chromatin structure are affected by covalent modifications of histone proteins and by non-histone binding proteins. Several classes of enzymes are known which modify histones at various sites.

There are a total of six classes of histones (HI, H2A, H2B, H3, H4, and H5) organized into two groups: core histones (H2A, H2B, H3, and H4) and linker histones (HI and H5). The basic unit of chromatin is the nucleosome, which consists of about 147 base pairs of DNA wrapped around the core histone octamer, consisting of two copies each of the core histones H2A, H2B, H3, and H4.

Basic nucleosome units are then further organized and condensed by the aggregation and folding of nucleosomes to form a highly condensed chromatin structure. A range of different states of condensation are possible, and the tightness of chromatin structure varies during the cell cycle, being most compact during the process of cell division.

Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications are acetylation, methylation, phosphorylation, ribosylation sumoylation, ubiquitination, citrullination, deimination, and biotinylation. The core of histones H2A and H3 can also be modified. Histone modifications are integral to diverse biological processes such as gene regulation, DNA repair, and chromosome condensation.

Histone methylation is one of the most important chromatin marks; these play important roles in transcriptional regulation, DNA-damage response, heterochromatin formation and maintenance, and X-chromosome inactivation. A recent discovery also revealed that histone methylation affects the splicing outcome of pre-mRNA by influencing the recruitment of splicing regulators. Histone methylation includes mono-, di-, and tri-methylation of lysines, and mono-, symmetric di-, and asymmetric di-methylation of arginines. These modifications can be either an activating or repressing mark, depending on the site and degree of methylation.

Histone Demethylases

A "demethylase" or "protein demethylase," as referred to herein, refers to an enzyme that removes at least one methyl group from polypeptide. Demethylases comprise a JmjC domain, and can be a methyl-lysine or methyl-arginine demethylase. Some demethylases act on histones, e.g., act as a histone H3 or H4 demethylase. For example, an H3 demethylase may demethylate one or more of H3K4, H3K9, H3K27, H3K36 and/or H3K79. Alternately, an H4 demethylase may demethylate histone H4K20. Demethylases are known which can demethylate either a mono-, di- and/or a tri-methylated substrate. Further, histone demethylases can act on a methylated core histone substrate, a mononucleosome substrate, a dinucleosome substrate and/or an oligonucleosome substrate, peptide substrate and/or chromatin (e.g., in a cell-based assay).

The first lysine demethylase discovered was lysine specific demethylase 1 (LSD1/KDM1), which demethylates both mono- and di-methylated H3K4 or H3K9, using flavin as a cofactor. A second class of Jumonji C (JmjC) domain containing histone demthylases were predicted, and confirmed when a H3K36 demethylase was found used a formaldehyde release assay, which was named JmjC domain containing histone demethylase 1 (JHDM1/KDM2A).

More JmjC domain-containing proteins were subsequently identified and they can be phylogenetically clustered into seven subfamilies: JHDM1, JHDM2, JHDM3, JMJD2, JARID, PHF2/PHF8, UTX/UTY, and JmjC domain only.
LSD-1

Lysine-specific demethylase 1 (LSD1) is a histone lysine demethylase that specifically demethylates monomethylated and dimethylated histone H3 at K4 and also demethylates dimethylated histone H3 at K9. Although the main target of LSD1 appears to be mono- and di-methylated histone lysines, specifically H3K4 and H3K9, there is evidence in the literature that LSD1 can demethylate methylated lysines on non-histone proteins like p53, E2F1, Dnmt1 and STAT3.

LSD1 has a fair degree of structural similarity and amino acid identity/homology to polyamine oxidases and monoamine oxidases, all of which (i.e., MAO-A, MAO-B and LSD1) are flavin dependent amine oxidases which catalyze the oxidation of nitrogen-hydrogen bonds and/or nitrogen-carbon bonds. LSD1 also includes an N-terminal SWRIM domain. There are two transcript variants of LSD1 produced by alternative splicing.

In some embodiments, 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile is capable of inhibiting LSD1 activity in a biological sample by contacting the biological sample with 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile. In some embodiments, 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile is capable of modulating the level of histone 3 lysine 4 methylation in the biological sample. In some embodiments, 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile is capable of modulating histone-3 lysine-9 methylation levels in the biological sample.

One embodiment provides a method of treating cancer in a patient in need thereof, comprising administering to the patient the compound 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, or a pharmaceutically acceptable salt thereof. One embodiment provides a method of treating cancer in a patient in need thereof, comprising administering to the patient the compound 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, or a pharmaceutically acceptable salt thereof. One embodiment provides a method of treating cancer in a patient in need thereof, comprising administering to the patient a composition comprising 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, or a pharmaceutically acceptable salt thereof. Another embodiment provides a method of treating cancer in a patient in need thereof, comprising administering to the patient a composition comprising 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate. In a further embodiment is the method for treating cancer in a subject wherein the cancer is selected from breast cancer, lung cancer, prostate cancer, glioblastoma, and leukemia. In a further embodiment is the method for treating cancer in a subject wherein the cancer is selected from acute myeloid leukemia (AML), acute lymphoblastic leukemia (ALL), small cell lung cancer (SCLC), non-small cell lung cancer (NSCLC), neuroblastoma, small round blue cell tumors, glioblastoma, or ER(−) breast cancer.

4-[2-(4-amino-piperidin-1-yl)-5-(3-fluoro-4-methoxy-phenyl)-1-methyl-6-oxo-1,6-dihydro-pyrimidin-4-yl]-2-fluoro-benzonitrile The term "4-[2-(4-amino-piperidin-1-yl)-5-(3-fluoro-4-methoxy-phenyl)-1-methyl-6-oxo-1,6-dihydro-pyrimidin-4-yl]-2-fluoro-benzonitrile" refers to the compound with the following structure:

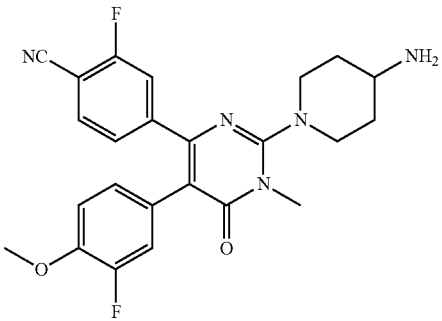 [SMILES: COc1ccc(-c2c(-c3ccc(C#N)c(F)c3)nc(N3CCC(N)CC3)n(C)c2=O)cc1F]

4-[2-(4-amino-piperidin-1-yl)-5-(3-fluoro-4-methoxy-phenyl)-1-methyl-6-oxo-1,6-dihydro-pyrimidin-4-yl]-2-fluoro-benzonitrile is described in U.S. patent application Ser. No. 14/701,304.

Pharmaceutically acceptable salts of 4-[2-(4-amino-piperidin-1-yl)-5-(3-fluoro-4-methoxy-phenyl)-1-methyl-6-oxo-1,6-dihydro-pyrimidin-4-yl]-2-fluoro-benzonitrile include, but are not limited to, acid addition salts, formed by reacting the compound with a pharmaceutically acceptable inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like.

In some embodiments, described herein is a pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile. In some embodiments, described herein is a pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, wherein the pharmaceutically acceptable salt is a p-toluene sulfonic acid salt (also known as tosylate), sulfuric acid salt, methanesulfonic acid salt (also known as mesylate), benzenesulfonic acid salt (also known as besylate), phosphoric acid salt, or benzoic acid salt. In some embodiments, described herein is a pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, wherein the pharmaceutically acceptable salt is the p-toluene sulfonic acid salt. In some embodiments, described herein is a pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, wherein the pharmaceutically acceptable salt is the sulfuric acid salt. In some embodiments, described herein is a pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, wherein the pharmaceutically acceptable salt is the methanesulfonic acid salt. In some embodiments, described herein is a pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, wherein the pharmaceutically acceptable salt is the benzenesulfonic acid salt. In some embodiments, described herein is a pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, wherein the pharmaceutically acceptable salt is the phosphoric acid salt. In some embodiments, described herein is a pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, wherein the pharmaceutically acceptable salt is the benzoic acid salt.

Amorphous Phase

In some embodiments, 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt is amorphous. In some embodiments, the amorphous phase of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt has an XRPD pattern showing a lack of crystallinity.

Form 1

In some embodiments, 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt is crystalline. In some embodiments, described herein is a crystalline Form 1 of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt. In some embodiments, Form 1 of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt is characterized as having:

(a) an X-Ray powder diffraction (XRPD) pattern substantially the same as shown in FIG. 1;
(b) an X-ray powder diffraction (XRPD) pattern with characteristic peaks at 4.9° 2-Theta, 9.7° 2-Theta, 13.4° 2-Theta, 18.0° 2-Theta, 18.5° 2-Theta;
(c) a DSC thermogram with an endotherm having an onset temperature at about 317° C.;
(d) a DSC thermogram substantially similar to the one set forth in FIG. 2; or
(e) combinations thereof.

In some embodiments, Form 1 has an X-Ray powder diffraction (XRPD) pattern substantially the same as shown in FIG. 1.

In some embodiments, Form 1 has an X-ray powder diffraction (XRPD) pattern with characteristic peaks at 4.9° 2-Theta, 9.7° 2-Theta, 13.4° 2-Theta, 18.0° 2-Theta, 18.5° 2-Theta.

In some embodiments, Form 1 has substantially the same X-ray powder diffraction (XRPD) pattern post storage at 40° C. and 75% RH for at least a week.

In some embodiments, Form 1 has substantially the same X-ray powder diffraction (XRPD) pattern post storage at 25° C. and 96% RH for at least a week.

In some embodiments, Form 1 has a DSC thermogram with an endotherm having an onset temperature at about 317° C.

Figure 2:
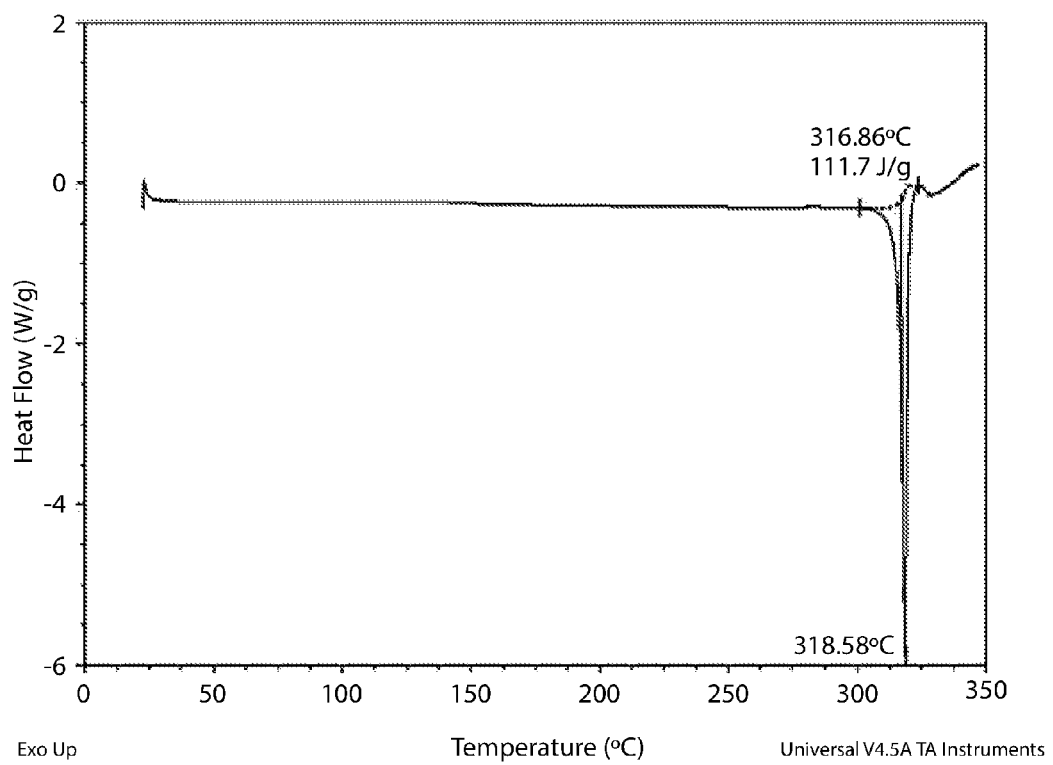
FIG. 2 illustrates the DSC thermogram of Form 1 of crystalline 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt.

In some embodiments, Form 1 has a DSC thermogram substantially similar to the one set forth in FIG. 2.

In some embodiments, Form 1 is characterized as having properties (a), (b), (c), and (d), or any combination thereof.

Preparation of Crystalline Forms

In some embodiments, a crystalline form of a pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, such as 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate, is prepared as outlined in the Examples. It is noted that solvents, temperatures and other reaction conditions presented herein may vary.

Suitable Solvents

Therapeutic agents that are administrable to mammals, such as humans, must be prepared by following regulatory guidelines. Such government regulated guidelines are referred to as Good Manufacturing Practice (GMP). GMP guidelines outline acceptable contamination levels of active therapeutic agents, such as, for example, the amount of residual solvent in the final product. Preferred solvents are those that are suitable for use in GMP facilities and consistent with industrial safety concerns. Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005).

Solvents are categorized into three classes. Class 1 solvents are toxic and are to be avoided. Class 2 solvents are solvents to be limited in use during the manufacture of the therapeutic agent. Class 3 solvents are solvents with low toxic potential and of lower risk to human health. Data for Class 3 solvents indicate that they are less toxic in acute or short-term studies and negative in genotoxicity studies.

Class 1 solvents, which are to be avoided, include: benzene; carbon tetrachloride; 1,2-dichloroethane; 1,1-dichloroethene; and 1,1,1-trichloroethane.

Examples of Class 2 solvents are: acetonitrile, chlorobenzene, chloroform, cyclohexane, 1,2-dichloroethene, dichloromethane, 1,2-dimethoxyethane, N,N-dimethyl-acetamide, N,N di-methylformamide, 1,4-dioxane, 2-ethoxyethanol, ethyleneglycol, formamide, hexane, methanol, 2-methoxyethanol, methylbutyl ketone, methylcyclohexane, N-methylpyrrolidine, nitromethane, pyridine, sulfolane, tetralin, toluene, 1,1,2-trichloroethene and xylene.

Class 3 solvents, which possess low toxicity, include: acetic acid, acetone, anisole, 1-butanol, 2-butanol, butyl acetate, tert-butylmethyl ether (MTBE), cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran.

In some embodiments, compositions comprising a crystalline form of a pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, such as 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate, include a residual amount of an organic solvent(s). In some embodiments, compositions comprising a crystalline form of a pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, such as 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate, include a detectable amount of an organic solvent(s). In some embodiments, compositions comprising a crystalline form of a pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, such as 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate, include a residual amount of a Class 3 solvent. In some embodiments, the organic solvent is a Class 3 solvent. In some embodiments, the Class 3 solvent is selected from the group consisting of acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran. In some embodiments, the Class 3 solvent is ethanol.

The methods and compositions described herein include the use of a crystalline form of a pharmaceutically acceptable salt 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, such as 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate. In addition, the crystalline forms of the pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, such as 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate, can exist in unsolvated as well as solvated forms with pharmaceutically acceptable solvents such as water, ethanol, and the like.

Certain Terminology

The term "cancer" as used herein refers to an abnormal growth of cells which tend to proliferate in an uncontrolled way and, in some cases, to metastasize (spread).

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, delaying progression of condition, relieving a condition caused by the disease or condition, or stopping the symptoms of the disease or condition either prophylactically and/or therapeutically. In some embodiments, treatment includes extending progression-free survival. In some embodiments, treatment includes reducing the relative risk of disease progression compared to other treatment options.

The term "progression-free survival" is the amount of time during and after the treatment of a disease, such as cancer, that a patient lives with the disease but it does not get worse. In a clinical trial, measuring progression-free survival is one technique to determine the efficacy of the treatment.

The term "pharmaceutically acceptable excipient," as used herein, refers to a material, such as a carrier, diluent, stabilizer, dispersing agent, suspending agent, thickening agent, etc. which allows processing the active pharmaceutical ingredient (API) into a form suitable for administration to a mammal. In one aspect, the mammal is a human. Pharmaceutically acceptable excipients refer to materials which do not substantially abrogate the desired biological activity or desired properties of the compound (i.e., API), and is relatively nontoxic, i.e., the material is administered to an individual without causing undesirable biological effects or interacting in a deleterious manner with any of the components of the composition in which it is contained.

"Active pharmaceutical ingredient" or API refers to a compound that possesses a desired biological activity or desired properties. In some embodiments, an API is a crystalline form of a pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, such as 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate. In some embodiments, the API is crystalline 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate. In some embodiments, the API has a purity of greater than 90%, greater than 95%, greater than 96%, greater than 97%, greater than 98%, greater than 98%, or greater than 99%.

The term "pharmaceutical composition" refers to a mixture of a crystalline form of a pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, such as 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate, with other chemical components, such as carriers, stabilizers, diluents, dispersing agents, suspending agents, thickening agents, excipients, etc. The pharmaceutical composition facilitates administration of the compound to a mammal.

"Detectable amount" refers to an amount that is measurable using standard analytic methods (e.g. ion chromatography, mass spectrometry, NMR, HPLC, gas chromatography, elemental analysis, IR spectroscopy, inductively coupled plasma atomic emission spectrometry, USP<231>Method II, etc) (ICH guidances, *Q2A Text on Validation of Analytical Procedures* (March 1995) and *Q2B Validation of Analytical Procedures: Methodology* (November 1996)).

The term "acceptable" with respect to a formulation, composition or ingredient, as used herein, means having no persistent detrimental effect on the general health of the subject being treated.

The terms "effective amount" or "therapeutically effective amount," as used herein, refer to a sufficient amount of an agent being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. The term "therapeutically effective amount" includes, for example, a prophylactically effective amount. The effective amount will be selected based on the particular patient and the disease level. It is understood that "an effect amount" or "a therapeutically effective amount" varies from subject to subject, due to variation in metabolism of drug, age, weight, general condition of the subject, the condition being treated, the severity of the condition being treated, and the judgment of the prescribing physician. In one embodiment, an appropriate "effective" amount in any individual case is determined using techniques, such as a dose escalation study.

The terms "kit" and "article of manufacture" are used as synonyms.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target. The term "subject" or "patient" encompasses mammals. In one aspect, the mammal is a human.

Pharmaceutical Compositions/Formulations

Pharmaceutical compositions are formulated using one or more physiologically acceptable carriers comprising excipients and auxiliaries which facilitate processing of the active compounds into preparations which are used pharmaceutically. Suitable techniques, carriers, and excipients include, but are not limited to, those found within, for example, *Remington: The Science and Practice of Pharmacy*, Nineteenth Ed (Easton, Pa.: Mack Publishing Co., 1995); Hoover, John E., *Remington's Pharmaceutical Sciences* (Mack Publishing Co., Easton, Pa. 1975); Liberman, H. A. and Lachman, L., Eds., *Pharmaceutical Dosage Forms* (Marcel Decker, New York, N.Y., 1980); and *Pharmaceutical Dosage Forms and Drug Delivery Systems*, Seventh Ed. (Lippincott Williams & Wilkins 1999), herein incorporated by reference in their entirety.

In some embodiments, a crystalline form of a pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, such as 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate, is formulated for oral administration to a mammal. In some embodiments, a crystalline form of a pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, such as 4-[2-(4-amino-piperidin-1-yl)-5-(3-fluoro-4-methoxy-phenyl)-1-methyl-6-oxo-1,6-dihydro-pyrimidin-4-yl]-2-fluoro-benzonitrile besylate, is formulated into an oral dosage form. In some embodiments, a crystalline form of a pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, such as 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate, is formulated into a solid oral dosage form. In some embodiments, a crystalline form of a pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, such as 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate, is formulated into a tablet, powder, pill, capsule, and the like, for oral ingestion by a mammal.

Contemplated pharmaceutical compositions provide a therapeutically effective amount of a crystalline form of a pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, such as 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate, enabling, for example, once-a-day, twice-a-day, three times a day, etc. administration. In one aspect, pharmaceutical compositions provide an effective amount of a crystalline form of a pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, such as 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate, enabling once-a-day dosing.

Dose Amounts

In one embodiment, the daily dosages appropriate for a crystalline form of a pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, such as 4-[2-(4-amino-piperidin-1-yl)-5-(3-fluoro-4-methoxy-phenyl)-1-methyl-6-oxo-1,6-dihydro-pyrimidin-4-yl]-2-fluoro-benzonitrile besylate, is from about 1 to about 30 mg/kg per body weight.

Kits/Articles of Manufacture

For use in the therapeutic methods of use described herein, kits/articles of manufacture are also described herein. Such kits include a carrier, package, or container that is optionally compartmentalized to receive one or more doses of a pharmaceutical composition of a crystalline form of a pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, such as 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate, for use in a method described herein. The kits provided herein contain packaging materials. Packaging materials for use in packaging pharmaceutical products include, but are not limited to those described in e.g., U.S. Pat. No. 5,323,907. Examples of pharmaceutical packaging materials include, but are not limited to, blister packs, bottles, tubes, bags, containers, bottles, and any packaging material suitable for a selected formulation and intended mode of administration and treatment. A wide array of formulations of a crystalline form of a pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, such as 4-[2-(4-amino-piperidin-1-yl)-5-(3-fluoro-4-methoxy-phenyl)-1-methyl-6-oxo-1,6-dihydro-pyrimidin-4-yl]-2-fluoro-benzonitrile besylate, and compositions thereof are contemplated, as are a variety of treatments for any disease, disorder, or condition that would benefit by treatment with an LSD-1 inhibitor.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a crystalline form of a pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, such as 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate, formulated in a compatible pharmaceutical carrier are also prepared, placed in an appropriate container, and labeled for treatment of an indicated condition.

EXAMPLES

Methods
X-Ray Powder Diffraction (XRPD)
Bruker AXS C2 GADDS

X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm.

The beam divergence, i.e., the effective size of the X-ray beam on the sample, was approximately 4 mm. A θ-θ continuous scan mode was employed with a sample-detector distance of 20 cm that gives an effective 2θ range of 3.2°-29.7°. Typically, the sample was exposed to the X-ray beam for 120 seconds. The software used for data collection was GADDS for XP/2000 4.1.43 and the data were analysed and presented using Diffrac Plus EVA v15.0.0.0.

Ambient Conditions

All samples (damp or dry) were run under ambient conditions as flat specimens. Approximately 1-2 mg of the sample was lightly pressed on a glass slide to obtain a flat surface.

Non-Ambient Conditions (Variable Temperature Experiments)

Samples run under non-ambient conditions were mounted on a silicon wafer with heat-conducting compound. The sample was then heated to the appropriate temperature at 10° C./min and subsequently held isothermally for 1 minute before data collection was initiated.

Bruker AXS D8 Advance

High resolution X-Ray Powder diffraction patterns were collected on a Bruker D8 diffractometer using Cu Kα radiation (40 kV, 40 mA), θ-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.6.1 and the data were analyzed and presented using Diffrac Plus EVA v15.0.0.0.

Samples were run under ambient conditions as flat plate specimens using powder as received. The sample was gently packed into a cavity cut into polished, zero-background (510) silicon wafer. The sample was rotated in its own plane during analysis. The details of the data collection are:

Angular range: 2 to 42° 2θ
Step size: 0.05° 2θ
Collection time: 0.5 s/step

Nuclear Magnetic Resonance (NMR)

NMR spectra were collected on a Bruker 400 MHz instrument equipped with an auto-sampler and controlled by a DRX400 console. Automated experiments were acquired using ICON-NMR v4.0.7 running with Topspin v1.3 using the standard Bruker loaded experiments. Samples were prepared in DMSO-$d_6$ and off-line analysis was carried out using ACD Spectrus Processor 2012.

Differential Scanning Calorimetry (DSC)

DSC data were collected on a Mettler DSC 823E equipped with a 34 position auto-sampler. The instrument was calibrated for energy and temperature using certified indium. Typically, 0.9-6 mg of each sample, in a pin-holed aluminum pan, was heated at 10° C./min from 25° C. to 350° C. A nitrogen purge at 50 ml/min was maintained over the sample. The instrument control and data analysis software was STARe v12.1.

Thermo-Gravimetric Analysis (TGA)

TGA data were collected on a TA Instruments Q500 TGA, equipped with a sixteen-position auto-sampler. The instrument was temperature calibrated using certified Alumel and Nickel. Typically, 8 mg-11 mg of each sample was loaded onto a pre-tared aluminum DSC pan and heated at 10° C./min from ambient temperature to 350° C. A nitrogen purge at 60 ml/min was maintained over the sample. The instrument control software was Advantage for Q Series v2.5.0.256 and Thermal Advantage v5.5.3 and the data were analyzed using Universal Analysis v4.5A.

Water Determination by Karl Fischer Titration (KF)

The water content of each sample was measured on a Metrohm 874 Oven Sample Processor at 150° C. with 851 Titrano Coulometer using Hydranal Coulomat AG oven reagent and nitrogen purge. Weighed solid samples were introduced into a sealed sample vial. Approx 10 mg of sample was used per titration and duplicate determinations were made. Data collection and analysis using Tiamo v2.2.

Chloride Content Determination by Titrimetric Analysis

The method for the analysis of chloride is by oxygen flask combustion of the sample. Once the combustion and absorption into solution has occurred, the samples were titrated using a calibrated Mercuric Nitrate solution. The samples are analyzed together with a blank and organic analytical standard reagents to ensure accuracy. The accuracy with this method is ±0.3% absolute with a detection limit of 0.10%.

Chemical Purity Determination by HPLC

Purity analysis was performed on an Agilent HP1100 series system equipped with a diode array detector and using ChemStation software vB.04.03 using the method detailed below:

TABLE 1

HPLC method for chemical purity determinations

| Parameter | Value |
| --- | --- |
| Sample Preparation | ~0.3 mg/ml in acetonitrile:water 1:1 |
| Column | Supelco Ascentis Express C18, 100 × 4.6 mm, 2.7 μm |
| Column Temperature (° C.) | 25 |
| Injection (μl) | 3 |
| Wavelength, Bandwidths (nm) | 255, 90 |
| Flow Rate (ml/min) | 2 |
| Phase A | 0.1% TFA in water |
| Phase B | 0.085% TFA in acetonitrile |

| | Time (min) | % Phase A | % Phase B |
| --- | --- | --- | --- |
| Timetable | 0 | 95 | 5 |
| | 6 | 5 | 95 |
| | 6.2 | 95 | 5 |
| | 8 | 95 | 5 |

Gravimetric Vapour Sorption (GVS)

Sorption isotherms were obtained using a SMS DVS Intrinsic moisture sorption analyser, controlled by DVS Intrinsic Control software v1.0.1.2 (or v 1.0.1.3). The sample temperature was maintained at 25° C. by the instrument controls. The humidity was controlled by mixing streams of dry and wet nitrogen, with a total flow rate of 200 ml/min. The relative humidity was measured by a calibrated Rotronic probe (dynamic range of 1.0-100% RH), located near the sample. The weight change, (mass relaxation) of the sample as a function of % RH was constantly monitored by the microbalance (accuracy ±0.005 mg).

Approximately 13 mg of sample was placed in a tared mesh stainless steel basket under ambient conditions. The sample was loaded and unloaded at 40% RH and 25° C. (typical room conditions). A moisture sorption isotherm was performed as outlined below (two scans giving one complete cycle). The standard isotherm was performed at 25° C. at 10% RH intervals over a 0-90% RH range. Data analysis was carried out using Microsoft Excel using DVS Analysis Suite v6.2 (or 6.1 or 6.0). The sample was recovered after completion of the isotherm and re-analyzed by XRPD.

TABLE 2

Method for SMS DVS Intrinsic experiments

| Parameter | Value |
| --- | --- |
| Adsorption - Scan 1 | 40-90 |
| Desorption/Adsorption - Scan 2 | 90-0, 0-40 |
| Intervals (% RH) | 10 |

TABLE 2-continued

Method for SMS DVS Intrinsic experiments

| Parameter | Value |
| --- | --- |
| Number of Scans | 4 |
| Flow rate (ml/min) | 200 |
| Temperature (° C.) | 25 |
| Stability (° C./min) | 0.2 |
| Sorption Time (hours) | 6 hour time out | pKa Determination and Prediction

Data were collected on a Sirius GLpKa instrument with a D-PAS attachment. Measurements were made at 25° C. in methanol/water mixtures by potentiometry. The titration media was ionic-strength adjusted (ISA) with 0.15 M KCl (aq). The values found in the methanol/water mixtures were corrected to 0% co-solvent via a Yasuda-Shedlovsky extrapolation. The data were refined using Refinement Pro software v2.2.3. Prediction of pKa values was made using ACD/Labs Percepta 2012.

Log P Determination and Prediction

Data were collected by potentiometric titration on a Sirius GLpKa instrument using three ratios of octanol:ionic-strength adjusted (ISA) water to generate Log P, Log Pion, and Log D values. The data were refined using Refinement Pro software v2.2.3. Prediction of Log P values was made using ACD/Labs Percepta 2012.

Thermodynamic Solubility in FeSSiF

Solubility was Determined by Suspending Sufficient Compound in Fed State Simulated intestinal fluid (FeSSIF) to give a maximum final concentration of >3 mg/ml of the parent free-form of the compound. The suspension was equilibrated at 25° C. for 24 hours then the pH was measured. The suspension was then filtered through a glass fibre C filter. The residue was analysed by XRPD as a damp solid. The filtrate was diluted by an appropriate factor prior to analysis by HPLC. Quantitation by HPLC was performed with reference to a standard solution of approximately 0.2 mg/ml in DMSO. Different volumes of the standard, diluted and undiluted sample solutions were injected. The solubility was calculated using the peak areas determined by integration of the peak found at the same retention time as the principal peak in the standard injection. Analysis was performed on an Agilent HP1100 series system equipped with a diode array detector and using ChemStation software vB.04.03.

TABLE 3

HPLC method for thermodynamic solubility measurements

| Parameter | Value |
| --- | --- |
| Type of method | Reverse phase with gradient elution |
| Column | Phenomenex Luna, C18 (2) 5 μm 50 × 4.6 mm |
| Column Temperature (° C.) | 25 |
| Standard Injections (μl) | 1, 2, 3, 5, 7, 10 |
| Test Injections (μl) | 1, 2, 3, 10, 15, 20 |
| Detection: Wavelength, Bandwidth (nm) | 255, 90 |
| Flow Rate (ml/min) | 2 |
| Phase A | 0.1% TFA in water |
| Phase B | 0.085% TFA in acetonitrile |

| | Time (min) | % Phase A | % Phase B |
| --- | --- | --- | --- |
| Timetable | 0.0 | 95 | 5 |
| | 1.0 | 80 | 20 |

TABLE 3-continued

| HPLC method for thermodynamic solubility measurements | | |
|---|---|---|
| Parameter | Value | |
| | 2.3 | 5 | 95 |
| | 3.3 | 5 | 95 |
| | 3.5 | 95 | 5 |
| | 4.4 | 95 | 5 |

Ion Chromatography (IC)

Data were collected on a Metrohm 861 Advanced Compact IC using IC Net software v2.3. Accurately weighed samples were prepared as stock solutions in an appropriate dissolving solution and diluted appropriately prior to testing. Quantification was achieved by comparison with standard solutions of known concentration of the ion being analyzed.

TABLE 4

| IC method for anion chromatography | |
|---|---|
| Parameter | Value |
| Type of method | Anion exchange |
| Column | Metrosep A Supp 5-250 (4.0 × 250 mm) |
| Column Temperature (° C.) | Ambient |
| Injection (μl) | 10 |
| Detection | Conductivity detector |
| Flow Rate (ml/min) | 0.7 |
| Eluent | 3.2 mM sodium carbonate; 1.0 mM sodium hydrogen carbonate in a 5% acetone aqueous solution. |

Example 1: Salt Study of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile An investigation of salt forms was performed to discover crystalline, non-hygroscopic salt forms of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile suitable for use as a pharmaceutical product.

Characterization of Free Base and Monohydrochloride Salt

The 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile free base is crystalline and has HPLC purities >96%, showed a DSC endotherm at 203.5° C. ($\Delta H = -89$ J/g) and a solubility in FeSSIF of 0.28 mg/ml. DSC, TGA and KF analyses suggests this material contains loosely adsorbed water.

4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile hydrochloride was a weak crystalline monohydrochloride (HCl Form 1). The presence of amorphous content in the sample was inferred from the presence of a halo in the XRPD diffractogram and the possible recrystallization event in the DSC thermogram. The material was hygroscopic with a 14% uptake at 90% RH by GVS. A reversible hysteresis at 60%-90% RH by GVS was associated with the formation of a new hydrate form. Partial crystallization of a new form after 14 days storage at 40° C./75% RH was confirmed by XRPD. DSC endotherm at 290.6° C. ($\Delta H = -84$ J/g) coincides with the onset of degradation, thus the endotherm is not indicative of a pure sample melt. HPLC purity of 97.6% for the hydrochloride salt was comparable to the freebase while FeSSIF solubility was higher at 0.75 mg/ml.

Materials

Commercial chemicals and solvents were purchased from Aldrich or Fluka. Acid stock solutions used in the screen were made up as described in Table 5:

TABLE 5

| Stock solutions used in salt screen | | | |
|---|---|---|---|
| Counter-ion | Concentration | Solvent | 1.1 eq for 30 mg of API (μl) |
| p-Toluene sulfonic acid—pTSA | 1.0M | THF | 73 |
| Sulfuric acid—SO4 | 1.0M | THF | 73 |
| Methanesulfonic acid—MSA | 1.0M | THF | 73 |
| Benzenesulfonic acid—BSA | 1.0M | THF | 73 |
| Phosphoric acid—PHOA | 1.0M | THF | 73 |
| Malonic acid—MLNA | 1.0M | THF | 73 |
| L-Tartaric acid—TAR | 1.0M | THF | 73 |
| Fumaric acid—FUA | 0.5M | Methanol:THF (1:1) | 146 |
| Citric acid—CA | 1.0M | THF | 73 |
| L-Malic acid—MA | 1.0M | THF | 73 |
| Benzoic acid—BA | 1.0M | IPA | 73 |
| Succinic acid—SUCA | 1.0M | Methanol | 73 |

Salt Feasibility Assessment

Solubility assessment of the material was performed as follows: 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile free base (10 mg) was treated with increasing volumes of solvent until the material fully dissolved or until a maximum of 70 vol had been used. After each addition of solvent, the system was gently heated to 50° C. and then allowed to stand at room temperature for 5 min before the addition of a new aliquot of solvent.

To assess the feasibility for salt formation in different solvents, the samples from the solubility assessment were treated with 1.1 eq of p-Toluenesulfonic acid (25 al of IM acid solution in THF) at 50° C., held for 30 min then cooled down to 5° C. at 0.1° C./min. The samples were stirred at 5° C. for 12 hr, filtered or evaporated to dryness, and analyzed by XRPD.

IPA Screening Procedure

4-[2-(4-amino-piperidin-1-yl)-5-(3-fluoro-4-methoxyphenyl)-1-methyl-6-oxo-1,6-dihydro-pyrimidin-4-yl]-2-fluorobenzonitrile free base (30 mg) was suspended in 1.2 ml of IPA at 50° C. and 1.1 eq of counterion solution was added. The samples were stirred at this temperature for 30 min then cooled to 5° C. at 0.1° C./min. A stirring rate of 400 revolutions per minute (rpm) was used throughout the experiments. After remaining at 5° C. for up to 48 hr, the samples were rapidly heated to 50° C. held for 2 hr then cooled to room temperature. A control experiment with no added counter-ion was also performed. The solids were filtered at room temperature, dried under vacuum (30° C.) for up to 24 hr and analyzed by XRPD.

1,4-Dioxane Screening Procedure

4-[2-(4-amino-piperidin-1-yl)-5-(3-fluoro-4-methoxyphenyl)-1-methyl-6-oxo-1,6-dihydro-pyrimidin-4-yl]-2-fluorobenzonitrile free base (30 mg) was dissolved in 1.5 ml of 1,4-dioxane at 50° C. to give a saturated solution and 1.1 eq of counterion solution was added. The samples were stirred at this temperature for 30 min then cooled to 5° C. at 0.1° C./min. A stirring rate of 400 rpm was used throughout the experiment. After remaining at 5° C. for 18 hr, the samples were rapidly heated to 50° C. held for 2 hr then cooled to room temperature. Control experiment with no added counter-ion was performed. The solids were filtered at room temperature, dried under vacuum (30° C.) for 18 hr and initially analyzed by XRPD.

Dichloromethane Screening Procedure

4-[2-(4-amino-piperidin-1-yl)-5-(3-fluoro-4-methoxyphenyl)-1-methyl-6-oxo-1,6-dihydro-pyrimidin-4-yl]-2-fluorobenzonitrile free base (30 mg) was dissolved in 0.3 ml of dichloromethane at 35° C. and 1.1 eq of counterion solution was added. The samples were stirred at this temperature for 30 min then cooled to 5° C. at 0.1° C./min. A stirring rate of 400 rpm was used throughout the experiment. After remaining at 5° C. for 18 hr, the solids were filtered at room temperature, dried under vacuum (30° C.) for 72 hr or air-dried and analysed by XRPD. Control experiment with no added counterion was performed.

Summary of Results

XRPD results from the salt screen using procedures described above are summarized in Tables 6-10. Every new pattern was labelled with the counterion and a number, for example, methanesulfonic acid—MSA as MSA1, MSA 2.

TABLE 6

| Counter-ion | IPA screen | 1,4-dioxane screen | DCM screen |
| --- | --- | --- | --- |
| p-Toluene sulfonic acid—pTSA | pTSA 1 | pTSA 1 | pTSA 2 |
| Sulfuric acid—SO4 | SO4 1 | SO4 1 (poor crystallinity) | SO4 1 |
| Methanesulfonic acid—MSA | MSA 1 | MSA 1 (poor crystallinity) | MSA 2 |
| Benzenesulfonic acid—BSA | BSA 1 | BSA 1 | BSA 2 |
| Phosphoric acid—PHOA | PHOA 1 | PHOA 2 | PHOA 3 |
| Malonic acid—MLNA | MLNA 1 | MLNA 2 | MLNA 1 |
| L-Tartaric acid—TAR | TAR 1 (poor crystallinity) | Amorphous | Amorphous |
| Fumaric acid—FUA | FUA 1 | FUA 2 (poor crystallinity) | FUA 3 |
| Citric acid—CA | FB 1 (poor crystallinity) | CA 1 (poor crystallinity) | CA 2 |
| L-Malic acid—MA | MA 1 | MA 2 | MA 3 |
| Benzoic acid—BA | BA 1 | BA 2 | BA 2 |
| Succinic acid—SUCA | SUCA 1 | SUCA 2 | SUCA 3 |
| Control | FB 1 | FB 2 | FB 1 |

TABLE 7

| DSC | XPRD pattern | NMR and/or IC | Stability post storage at 40° C./75% RH | Solubility in FeSSiF (pH) XRPD of residue |
| --- | --- | --- | --- | --- |
| Endotherm 30.9° C. (ΔH = −14 J/g) Exotherm 168.2° C. (ΔH = 11 J/g) Endotherm 290.6° C. (ΔH = −84 J/g) | HCL 1 | Consistent with salt form 1 eq counterion (titrimetric analysis) | Extra peaks observed | 0.75 mg/ml (4.89) Amorphous |
| Endotherm 281.3° C. (ΔH = −74 J/g) | pTSA 1 | 1 eq counterion, 0.008 eq dioxane, consistent with salt form | No form change | 0.87 mg/ml (4.85) pTSA 1 |
| Endotherm 66.8° C. (ΔH = −48 J/g) Endotherm 95.4° C. (ΔH = −1 J/g) Endotherm 139.7° C. (ΔH = −13 J/g) Endotherms 239.6° C. (ΔH = −86 J/g) | pTSA 2 | 1 eq counterion consistent with salt form | Slight change in pattern | Not determined |
| Endotherms 237.2° C. (ΔH = −79 J/g) | SO4 1 | Consistent with salt form | No form change | Not determined |

TABLE 7-continued

| DSC | XPRD pattern | NMR and/or IC | Stability post storage at 40° C./75% RH | Solubility in FeSSiF (pH) XRPD of residue |
|---|---|---|---|---|
| Endotherms 302.7° C. ($\Delta H = -236$ J/g) | | | | |
| Endotherms 231.1° C. ($\Delta H = -59$ J/g) Endotherms 300.3° C. ($\Delta H = -161$ J/g) | | Consistent with salt form 1.1 eq counterion (IC) | Not determined | 0.72 mg/ml (4.53) Amorphous |
| Endotherm 315.3° C. ($\Delta H = -103$ J/g) | MSA 1 | 1 eq counterion, 0.06 eq IPA, consistent with salt form | No form change | 1.01 mg/ml (4.86) Largely amorphous |
| Endotherm 88.4° C. ($\Delta H = -2$ J/g) Endotherm 142.9° C. ($\Delta H = -31$ J/g) Endotherm 178.3° C. ($\Delta H = -70$ J/g) Endotherms 254.2° C. ($\Delta H = -72$ J/g) | MSA 2 | 1 eq counterion consistent with salt form | Extra peaks observed | Not determined |
| Endotherm 303.5° C. ($\Delta H = -109$ J/g) | BSA 1 | 1 eq counterion, 0.005 eq IPA, consistent with salt form | No form change | 0.84 mg/ml (4.86) BSA 1—poor crystallinity |
| Endotherm 89.4° C. ($\Delta H = -11$ J/g) Endotherm 122.8° C. ($\Delta H = -24$ J/g) Endotherms 253° C. ($\Delta H = -132$ J/g) | BSA 2 | 1 eq counterion consistent with salt formation | Extra peaks observed | Not determined |

TABLE 8

| DSC | XPRD pattern | NMR or IC | Stability post storage at 40° C./75% RH | Solubility in FeSSiF (pH) XRPD of residue |
|---|---|---|---|---|
| Endotherm 235.6° C. ($\Delta H = -132$ J/g) | PHOA 1 | 0.04 eq IPA, 1.1 eq counterion (IC) consistent with salt formation | No form change | 0.74 mg/ml (4.83) - for TE-1184-31-01 Amorphous |
| Endotherm 187.7° C. ($\Delta H = -16$ J/g) Endotherm 194.1° C. ($\Delta H = -15$ J/g) Endotherms 230.6° C. ($\Delta H = -102$ J/g) | PHOA 2 | 0.08 eq dioxane consistent with salt formation | Pattern change (poor crystallinity) | Not determined |
| Endotherms 61.9° C. ($\Delta H = -57$ J/g) Endotherm 165.7° C. ($\Delta H = -9$ J/g) Endotherm 181.3° C. ($\Delta H = -32$ J/g) Endotherms 227.3° C. ($\Delta H = -100$ J/g) | PHOA 3 | Peak shifts consistent with salt form | Reduced crystallinity | Not determined |
| Endotherm 29.7° C. ($\Delta H = -9$ J/g) Endotherms 172.2° C. ($\Delta H = -254$ J/g) | MLNA 1 | 1 eq counterion, 0.02 eq IPA consistent with salt formation | Pattern change (poor crystallinity) | Not determined |
| Endotherm 60.0° C. ($\Delta H = -14$ J/g) Endotherm 110.9° C. ($\Delta H = -19$ J/g) Exotherm 141.7° C. ($\Delta H = 15$ J/g) Endotherm 173.7° C. ($\Delta H = -196$ J/g) | MLNA 2 | Consistent with salt formation, 1 eq counterion, 0.35 eq dioxane | Pattern change | Not determined |
| Endotherm 28.9° C. ($\Delta H = -36$ J/g) Endotherms 175.5° C. ($\Delta H = -213$ J/g) | MLNA 1 | Not determined | Pattern change | Not determined |
| Endotherm 31.0° C. ($\Delta H = -43$ J/g) | TAR 1 (poor | Peak shifts consistent with salt form | Pattern change (poor crystallinity) | Not determined |

TABLE 8-continued

| DSC | XPRD pattern | NMR or IC | Stability post storage at 40° C./75% RH | Solubility in FeSSiF (pH) XRPD of residue |
|---|---|---|---|---|
| Endotherm 122.7° C. (ΔH = −11 J/g) Exotherm 158.8° C. (ΔH = 25 J/g) Endotherms 224.1° C. (ΔH = −159 J/g) | crystallinity) | | | |

TABLE 9

| DSC | XPRD pattern | NMR or IC | Stability post storage at 40° C./75% RH | Solubility in FeSSiF (pH) XRPD of residue |
|---|---|---|---|---|
| Endotherm 30.4° C. (ΔH = −44 J/g) Exotherm 154.5° C. (ΔH = 17 J/g) Endotherm 238.1° C. (ΔH = −149 J/g) | FUA 1 | 0.5 eq counterion, 0.3 eq IPA, consistent with salt formation; extra peaks at 3.57, 3.74-3.78 ppm | Pattern change (poor crystallinity) | Not determined |
| Endotherm 36.9° C. (ΔH = −43 J/g) Step changes 90° C.−140° C. Endotherm 239.3° C. (ΔH = −160 J/g) | FUA 2 | 0.5 eq counterion, 0.2 eq dioxane (overlaps with broad signal) consistent with salt formation | Increased crystallinity | Not determined |
| Endotherm 29.5° C. (ΔH = −33 J/g) Exotherm 180.8° C. (ΔH = 25 J/g) Endotherms 243.5° C. (ΔH = −135 J/g) | FUA 3 | 0.4 eq counterion, consistent with salt formation, extra peaks at 5.8, 6.1-6.7 ppm | Pattern change | Not determined |
| Endotherm 35.1° C. (ΔH = −7 J/g) Endotherm 126.3° C. (ΔH = −45 J/g) Endotherm 159.2° C. (ΔH = −109 J/g) | CA 1 | Consistent with salt formation, counterion peaks overlapping with solvent and parent signal | Pattern change | Not determined |
| Endotherm 35.5° C. (ΔH = −4 J/g) Endotherm 93.7° C. (ΔH = −21 J/g) Endotherm 168.8° C. (ΔH = −156 J/g) | CA 2 | Consistent with salt formation, counterion peaks overlapping with solvent and parent signal | No form change | Not determined |
| Endotherm 29.8° C. (ΔH = −21 J/g) Endotherm 157.3° C. (ΔH = −52 J/g) Exotherm 168.8° C. (ΔH = 44 J/g) Endotherm 212.8° C. (ΔH = −135 J/g) | MA 1 | Peak shifts consistent with salt formation, 0.5 eq IPA | Amorphous | 0.63 mg/ml (4.89) Amorphous |
| Multiple overlapping events from 30° C. to 240° C. | MA 2 | Peak shifts consistent with salt formation, 0.6 eq dioxane | Pattern change (poor crystallinity) | Not determined |
| Multiple overlapping events from 30° C. to 240° C. | MA 3 | Peak shifts consistent with salt formation | Pattern change | Not determined |

TABLE 10

| DSC | XPRD pattern | NMR or IC | Stability post storage at 40° C./75% RH | Solubility in FeSSiF (pH) XRPD of residue |
|---|---|---|---|---|
| Endotherm 231.9° C. (ΔH = −230 J/g) | BA 1 | 1 eq counterion, 0.32 eq IPA, consistent with salt formation | No significant change | 0.88 mg/ml (4.85) - for TE-1184-31-02 Poor crystallinity |

TABLE 10-continued

| DSC | XPRD pattern | NMR or IC | Stability post storage at 40° C./75% RH | Solubility in FeSSiF (pH) XRPD of residue |
|---|---|---|---|---|
| Exotherm 192.4° C. (ΔH = 5 J/g) Endotherm 234.9° C. (ΔH = −230 J/g) | BA 2 | 1 eq counterion, 0.03 eq dioxane consistent with salt formation | No significant change | Not determined |
| Endotherm 50.9° C. (ΔH = −37 J/g) Endotherm 177.8° C. (ΔH = −71 J/g) Endotherm 183.8° C. (ΔH = −31 J/g) | SUCA 1 | Peak shifts consistent with salt formation | Slight change in pattern | 0.96 mg/ml (4.89) Amorphous |
| Endotherm 41.0° C. (ΔH = −101.4 J/g) Endotherm 97.5° C. (ΔH = −7 J/g) Endotherm 185.3° C. (ΔH = −32 J/g) Endotherm 201.4° C. (ΔH = −69 J/g) | SUCA 2 | Peak shifts consistent with salt formation | Pattern change (poor crystallinity) | Not determined |
| Endotherm 32.3° C. (ΔH = −38 J/g) Endotherm 183.8° C. (ΔH = −61 J/g) | SUCA 3 | Peak shifts consistent with salt formation | Slight change in pattern | Not determined |

The screening experiments using three solvents (IPA, 1,4-dioxane and DCM) and twelve counterions gave twenty-six new solid forms.

One solid form (SO4-1) was isolated from screening using sulphuric acid in all three solvents. Experiments using tartaric acid only gave a crystalline form (TAR 1) with IPA and amorphous solids from 1, 4-dioxane and DCM screens. At least two solid forms were obtained for each of the remaining ten counterions.

Representative samples for the twenty-six forms were further analysed by NMR/IC and DSC. The stability of the samples after storage at 40° C./75% RH was also assessed by XRPD. Solubility in FeSSIF media was determined for selected samples. Tables 6-10 show a summary of the preliminary characterization of the new forms. NMR data for all forms showed peak shifts consistent with salt formation and where applicable the equivalence of counterion and solvent was obtained. IC was employed to determine the molar equivalence for inorganic counterions, sulphate and phosphate.

The onset temperature for DSC events gives indication of the thermal stability of the forms. pTSA 1, SO4 1, MSA 1, BSA 1, PHOA 1 and BA 1 samples show good thermal stability. The onsets of DSC events are greater than 200° C.; this data is consistent with non-solvated crystalline solids. The twenty remaining forms have thermal events occurring from as low as ~30° C. These may be solvated/hydrated forms.

The non-solvated forms remained unchanged by XRPD post storage at 40° C./75% RH while the other forms showed pattern changes. FeSSiF solubility for these six forms (0.72-1.01 mg/ml) is comparable to the HCl salt value of 0.74 mg/ml.

The following have been identified as having improved stability and solubility when compared to the HCl salt: pTSA 1, SO4-1, MSA 1, BSA1, PHOA 1, and BA 1.

Example 2: Preparation of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate

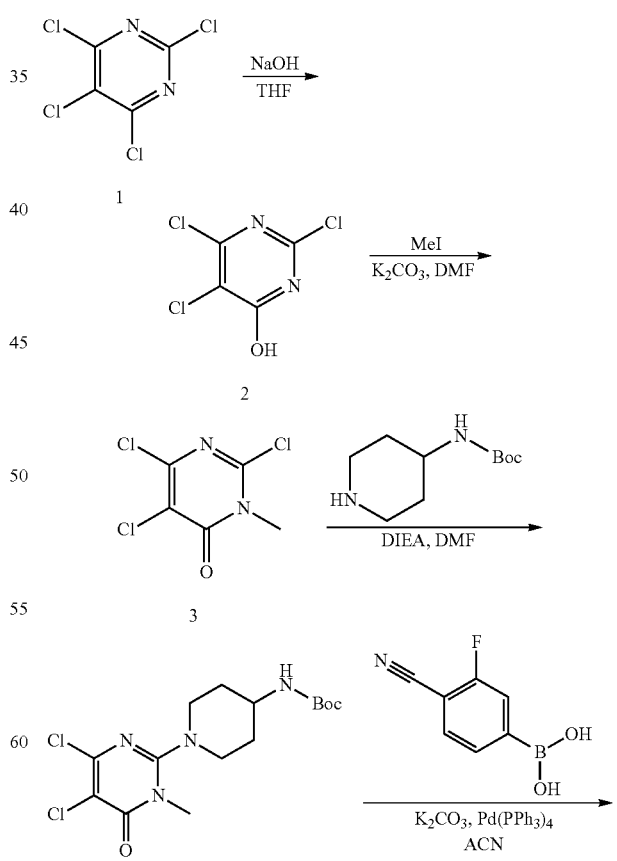

-continued

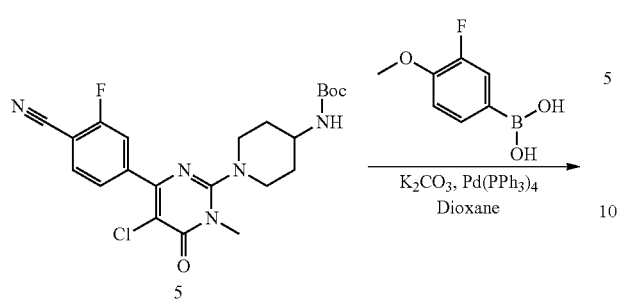

5

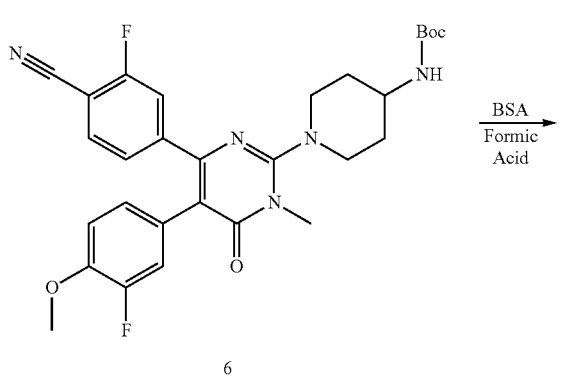

6

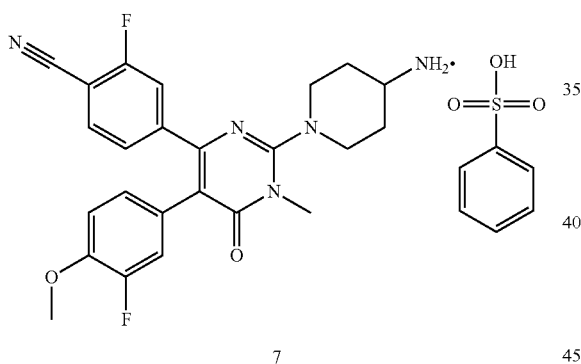

7

Step 1: Preparation of 2,5,6-trichloropyrimidin-4-ol

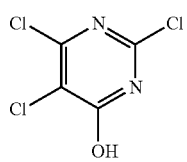

To a solution of 2,4,5,6-tetrachloropyrimidine (1 kg, 4.63 mol) in THF (6 L) was added 1N NaOH (6 L, 6.0 mol) dropwise, and the mixture was stirred overnight at room temperature. The solution was acidified with 1N HCl and extracted with DCM (3×). The combined organics were dried ($Na_2SO_4$) and concentrated in vacuo. The solids were slurried in $Et_2O$ for 30 min, filtered, washed with $Et_2O$ and dried to give 635 g (69%) of the title compound. LCMS (C18 column, column size: 4.6*50 mm; mobile phase: 20%-40%, Acetonitrile-Water-0.02% $NH_4OAc$): Rt=2.785 min; [M+H] Calc'd for $C_4HCl_3N_2O$, 199. Found, 199.

Step 2: Preparation of 2,5,6-trichloro-3-methyl-3-hydropyrimidin-4-one

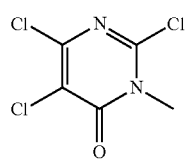

A solution of 2,5,6-trichloropyrimidin-4-ol (670 g, 3.38 mol) and $K_2CO_3$ (560 g, 4.06 mol) in DMF (5 L) was stirred at room temperature for 15 min and then cooled to 0° C. Iodomethane (528 g, 3.72 mol) was added dropwise and the mixture was stirred at room temperature for 17 hr. The reaction mixture was diluted with ethyl acetate, washed with brine, dried ($Na_2SO_4$) and concentrated in vacuo. The residue was purified by silica gel chromatography (PE:EA, 10:1) to give 447 g (62%) of the title compound. $^1$H NMR (400 MHz, $CDCl_3$): δ 3.74 (s, 3H). LCMS (C18 column; column size: 4.6*50 mm; mobile phase: 20%-95%, Acetonitrile-Water-0.02% $NH_4OAc$): Rt=2.986 min; [M+H] Calc'd for $C_5H_3Cl_3N_2O$, 213. Found, 213.

Step 3: Preparation of N-[1-(5,6-dichloro-3-methyl-4-oxo(3-hydropyrimidin-2-yl))(4-piperidyl)](tert-butoxy)carboxamide

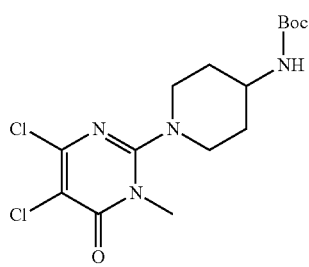 [SMILES: Cn1c(N2CCC(NC(=O)OC(C)(C)C)CC2)nc(Cl)c(Cl)c1=O]

A solution of 2,5,6-trichloro-3-methyl-3-hydropyrimidin-4-one (532 g, 2.51 mol), DIEA (648 g, 5.02 mol) and (tert-butoxy)-N-(4-piperidyl)carboxamide (502 g, 2.51 mol) in DMF (800 mL) was heated to 120° C. for 1 hr. The solvent was removed in vacuo and the residue was purified by silica gel chromatography (PE:EA, 1:1) to give 751 g (80%) of the title compound. $^1$H NMR (400 MHz, $CDCl_3$): δ 1.45 (s, 9H), 1.50-1.58 (m, 2H), 2.06-2.10 (m, 2H), 2.98-3.05 (m, 2H), 3.48 (s, 3H), 3.53-3.56 (m, 2H), 3.70 (s, 1H), 4.52 (s, 1H). LCMS (C18 column; column size: 4.6*50 mm; mobile phase: 20%-95%, Acetonitrile-Water-0.02% $NH_4OAc$): Rt=4.006 min; [M+H] Calc'd for $C_{15}H_{22}Cl_2N_4O_3$, 377. Found, 321 (MW-tBu).

Step 4: Preparation of tert-butyl 1-(5-chloro-4-(3-fluoro-4-cyanophenyl)-1-methyl-6-oxo-1,6-dihydro-pyrimidin-2-yl)piperidin-4-ylcarbamate

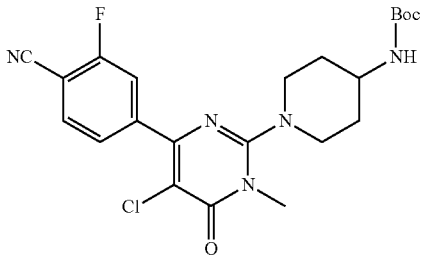 [SMILES: Cn1c(N2CCC(NC(=O)OC(C)(C)C)CC2)nc(-c2ccc(C#N)c(F)c2)c(Cl)c1=O]

To a solution of N-[1-(5,6-dichloro-3-methyl-4-oxo(3-hydropyrimidin-2-yl))(4-piperidyl)](tert-butoxy)carboxamide (150 g, 0.40 mol) in ACN (4 L), under $N_2$ atmosphere, was added 3-fluoro-4-cyanophenylboronic acid (65.8 g, 0.40 mol), Pd(Ph$_3$P)$_4$ (9.3 g, 8 mmol) and 0.4 N Na$_2$CO$_3$ (2 L, 0.80 mol). The mixture was stirred at 85° C. for 2 hr and was allowed to cool to room temperature. Water (2 L) was added, and the aqueous mixture was extracted with ethyl acetate (3×). The organics were combined, washed with water, washed with brine, dried (Na$_2$SO$_4$) and concentrated. The residue was purified by silica gel chromatography (PE:EA, 3:1) to give 95 g (57%) of the title compound. $^1$H NMR (400 MHz, CDCl$_3$): δ 1.45 (s, 9H), 1.54-1.61 (m, 2H), 2.05-2.13 (m, 2H), 2.99-3.08 (m, 2H), 3.53-3.58 (s, 5H), 3.70 (s, 1H), 4.54 (d, J=6.0 Hz, 1H), 7.68-7.80 (m, 3H). LCMS (C18 column; column size: 4.6*50 mm; mobile phase: 5%-95%, Acetonitrile-Water-0.1% TFA): Rt=4.443 min; [M+H] Calc'd for C$_{22}$H$_{25}$ClFN$_5$O$_3$, 462. Found, 462.

Step 5: Preparation of tert-butyl N-[1-[4-(4-cyano-3-fluorophenyl)-5-(3-fluoro-4-methoxyphenyl)-1-methyl-6-oxopyrimidin-2-yl]piperidin-4-yl]carbamate

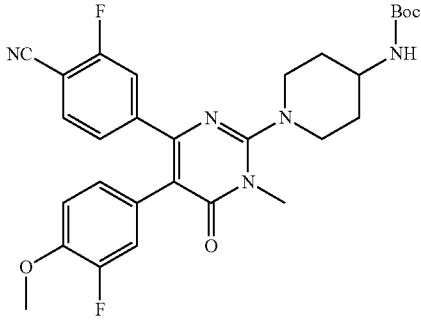 [SMILES: COc1ccc(-c2c(-c3ccc(C#N)c(F)c3)nc(N3CCC(NC(=O)OC(C)(C)C)CC3)n(C)c2=O)cc1F]

A mixture of (tert-butoxy)-N-{1-[5-chloro-6-(4-cyano-3-fluorophenyl)-3-methyl-4-oxo(3-hydropyrimidin-2-yl)](4-piperidyl)}carboxamide (295.8 g, 640 mmol), 3-fluoro-4-methoxy benzeneboronic acid (217.7 g, 1281 mmol), Pd(Ph$_3$P)$_4$ (18.5 g, 16.0 mmol) and K$_2$CO$_3$ (265.5 g, 1921 mmol) in degassed dioxane:H$_2$O (3:1, 3550 mL:887 mL) was stirred, under N$_2$ atmosphere, at 80° C. until reaction completion (at least 2 hr). The reaction mixture was allowed to cool to room temperature. Water (11 L) was added, and the slurry was stirred for 1 hr. The slurry was filtered, and the solids were washed with water (4 L) and washed with MeOH:Water (1:1, 4 L). The cake was stirred in MeOH (4 L) for 10 min. The slurry was filtered, and the solids were rinsed with MeOH (4 L) and washed with MTBE (4 L). The solids were taken in DCM (16 L), and the reaction mixture was stirred for 15 min. 2-mercaptoethyl ethyl sulfide silica (400 g) was then added, and the reaction mixture was stirred at room temperature, under N$_2$ atmosphere, for at least 1 hr. The reaction mixture was filtered through Celite in a frit filter, and the solids were rinsed with DCM (1 L). The volume of DCM filtrate was reduced to near dryness. MeOH (4 L) was added, and the solvent was reduced to dryness. The solids were taken in MeOH (4 L), and the slurry was cooled to 15° C. The slurry was filtered, and the cake was washed with MeOH (0.7 L), washed with MTBE (0.7 L) and dried to constant weight under vacuum at 45° C. to give 324.6 g (91.9%) of the title compound. $^1$H NMR (400 MHz, CDCl$_3$): δ 1.46 (s, 9H), 1.60 (d, J=10.11 Hz, 2H), 2.11 (d, J=11.62 Hz, 2H), 3.06 (t, J=12.00 Hz, 2H), 3.54 (s, 3H), 3.60 (d, J=13.64 Hz, 2H), 3.72 (br. s., 1H), 3.88 (s, 3H), 4.52 (br. s., 1H), 6.79-6.89 (m, 2H), 6.97 (d, J=12.38 Hz, 1H), 7.13 (d, J=8.34 Hz, 1H), 7.31 (d, J=9.85 Hz, 1H), 7.42 (br. s., 1H). LCMS (C18 column; column size: 4.6*50 mm; mobile phase: 5%-95%, Acetonitrile-Water-0.1% TFA): RT=6.979; [M+H] Calc'd for C$_{29}$H$_{31}$F$_2$N$_5$O$_4$, 552. Found, 552.

Step 6: Preparation of 4-[2-(4-amino-piperidin-1-yl)-5-(3-fluoro-4-methoxy-phenyl)-1-methyl-6-oxo-1,6-dihydro-pyrimidin-4-yl]-2-fluoro-benzonitrile, besylate salt

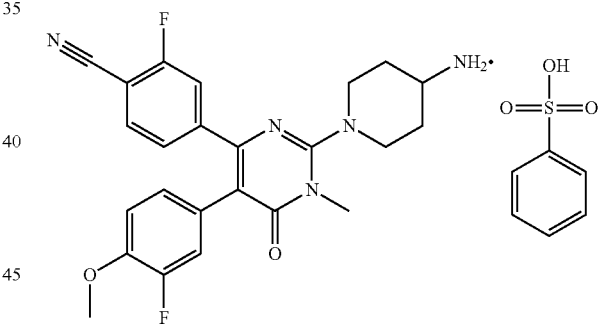

A solution of tert-butyl N-[1-[4-(4-cyano-3-fluorophenyl)-5-(3-fluoro-4-methoxyphenyl)-1-methyl-6-oxopyrimidin-2-yl]piperidin-4-yl]carbamate (5.0 g, 9.06 mmol) and benzenesulfonic acid monohydrate (1.9 g, 10.9 mmol) in formic acid (41.5 mL) was stirred at room temperature until reaction completion. The solution was filtered through a 0.45 μm filter. Water (25 mL) was added to the formic acid solution. Seeds of 4-[2-(4-amino-piperidin-1-yl)-5-(3-fluoro-4-methoxy-phenyl)-1-methyl-6-oxo-1,6-dihydro-pyrimidin-4-yl]-2-fluoro-benzonitrile, besylate salt (0.05 g) were introduced, and the solution was aged for 30 minutes. Water (up to 50 mL) was added to the mixture over 6 hr. The batch was then allowed to age for at least 12 hr. The batch was filtered, and the cake was washed with 80/20 Water/Formic Acid (v/v) and dried at 40-50° C. in a vacuum oven with a nitrogen bleed to give the (5.25 g, 95%) of title compound. $^1$H NMR (400 MHz, CD$_3$OD): δ 1.69 (q, 2H, J=11.4 Hz), 2.00 (d, 2H, J=10.2 Hz), 2.99 (t, 2H, J=12.3 Hz), 3.31 (bs, 1H), 3.42 (s, 3H), 3.72 (d, 2H, J=13.2 Hz), 3.81 (s, 3H), 6.78 (d, 1H, J=8.4 Hz), 7.01-7.06 (m, 1H), 7.04-7.06 (m, 1H), 7.19 (dd, 1H, 1.2 Hz), 7.32 (m, 2H), 7.32 (m, 1H), 7.46 (dd, 1H, J=10.5, 1.2 Hz), 7.61 (m, 2H), 7.82 (dd, 1H, J=8.1, 7.2 Hz), 7.92 (bs, 1H), 7.92 (bs, 2H). LCMS (Column: Agilent Zorbax SB-C8, 4.6×50 mm, 3.5 um particle size; mobile phase: 5%-95%, Acetonitrile-Water-0.1% TFA): RT=3.854; [M+H] Calc'd for $C_{24}H_{23}F_2N_5O_2$, 452. Found, 452. A second recrystalization from 80/20 water/formic acid was performed as described above to provide material greater than 99% pure as determined by LC analysis.

The DSC thermogram of the title compound is provided in FIG. 2.

The XRPD pattern of Form 1 of the title compound is provided in FIG. 1. Characteristic diffraction peaks include 4.9° 2-Theta, 9.7° 2-Theta, 13.4° 2-Theta, 18.0° 2-Theta and 18.5° 2-Theta.

Figure 3:
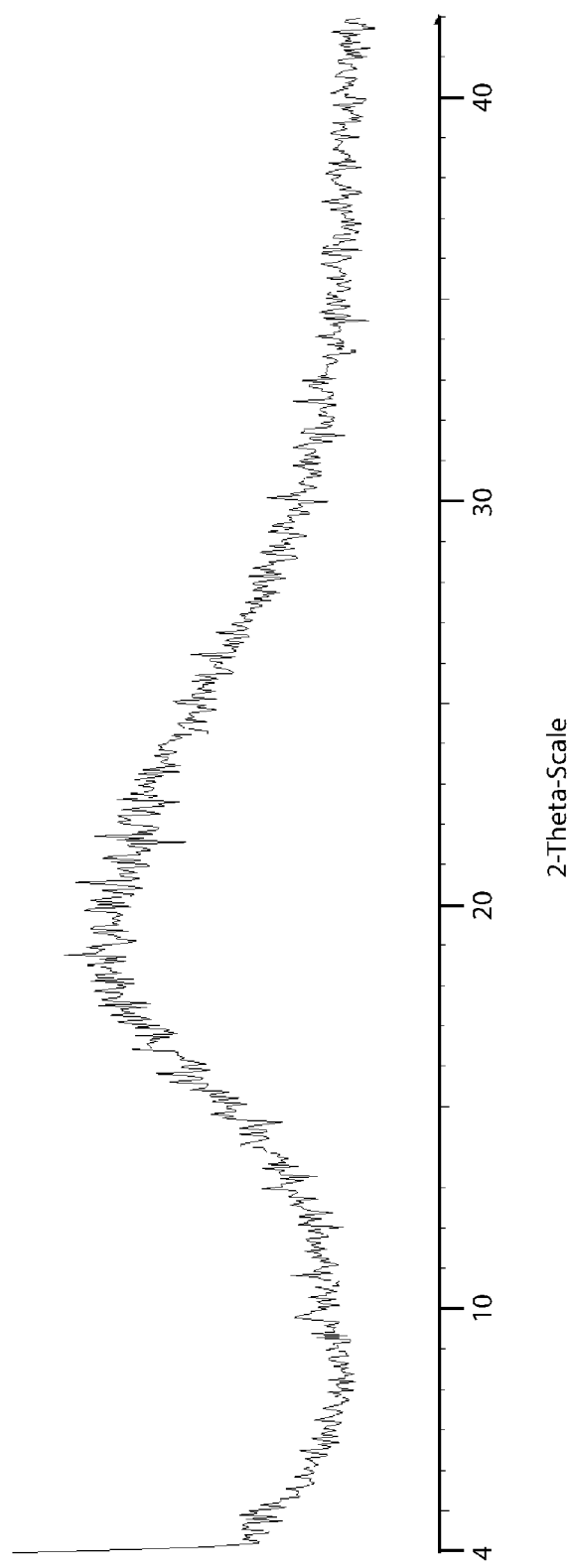
FIG. 3 illustrates the XRPD of amorphous crystalline 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt.

Example 3: Preparation of Amorphous 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate Amorphous 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate was prepared by ball milling Form 1 crystalline 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate for 99 min at 30 Hz. The resulting material was observed to be amorphous by XRPD analysis as shown in FIG. 3.

Example 4: Pharmaceutical Composition—Capsule Formulation

In one embodiment, capsule formulations of crystalline 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt for administration to humans are prepared with the following ingredients:

TABLE 11

Components of Capsule Formulation

| Component | Function | Quantity per Size 4 Capsule | Quantity per Size 1 Capsule |
| --- | --- | --- | --- |
| crystalline 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt | Active | 0.5 to 100 mg | 5 to 500 mg |
| Hypromellose, USP | Capsule Shell | 1 capsule | 1 capsule |

The process to prepare crystalline 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt in a capsule is as follows: Weigh the required amount of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt, add into the appropriate size capsule, and close capsule.

The examples and embodiments described herein are illustrative and various modifications or changes suggested to persons skilled in the art are to be included within this disclosure. As will be appreciated by those skilled in the art, the specific components listed in the above examples may be replaced with other functionally equivalent components, e.g., diluents, binders, lubricants, fillers, and the like.

What is claimed is:

1. A pharmaceutically acceptable salt of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile, wherein the pharmaceutically acceptable salt is in crystalline form.

2. The pharmaceutically acceptable salt of claim 1, wherein the pharmaceutically acceptable salt is a p-toluene sulfonic acid salt, sulfuric acid salt, methanesulfonic acid salt, benzenesulfonic acid salt, phosphoric acid salt, or benzoic acid salt.

3. The pharmaceutically acceptable salt of claim 1, wherein the pharmaceutically acceptable salt is a benzenesulfonic acid salt.

4. A crystalline form of 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt, designated Form 1, wherein the crystalline form that exhibits the following characteristics:
(a) an X-Ray powder diffraction (XRPD) pattern substantially the same as shown in FIG. 1;
(b) an XRPD pattern with characteristic peaks at 4.9° 2-Theta, 9.7° 2-Theta, 13.4° 2-Theta, 18.0° 2-Theta, and 18.5° 2-Theta;
(c) a DSC thermogram with an endotherm having an onset temperature at about 317° C.;
(d) a DSC thermogram substantially similar to the one set forth in FIG. 2; or
(e) combinations thereof.

5. The crystalline form of claim 4, wherein the crystalline form exhibits a characteristic XRPD pattern substantially the same as shown in FIG. 1.

6. The crystalline form of claim 4, wherein the crystalline form exhibits a characteristic XRPD pattern with characteristic peaks at 4.9° 2-Theta, 9.7° 2-Theta, 13.4° 2-Theta, 18.0° 2-Theta, and 18.5° 2-Theta.

7. The crystalline form of claim 4, wherein the crystalline form exhibits substantially the same characteristic XRPD pattern after storage at 40° C. and 75% RH for at least a week.

8. The crystalline form of claim 4, wherein the crystalline form exhibits substantially the same characteristic XRPD pattern after storage at 25° C. and 96% RH for at least a week.

9. The crystalline form of claim 4, wherein the crystalline form exhibits a DSC thermogram with an endotherm having an onset temperature at about 317° C.

10. A composition comprising a crystalline form of claim 1.

11. A pharmaceutical composition comprising the crystalline form of claim 1, and at least one pharmaceutically acceptable carrier, diluent, or excipient.

12. The pharmaceutical composition of claim 11, wherein the pharmaceutical composition is in an oral dosage form.

13. The pharmaceutical composition of claim 12, wherein the oral dosage form is a tablet, capsule or pill.

14. 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt that is in amorphous form.

15. A pharmaceutical composition comprising amorphous 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile besylate salt, and at least one pharmaceutically acceptable carrier, diluent, or excipient.

16. The pharmaceutical composition of claim 15, wherein the pharmaceutical composition is an oral dosage form.

17. The pharmaceutical composition of claim 16, wherein the oral dosage form is a tablet, capsule, or pill.

18. A pharmaceutical composition comprising the crystalline form of claim 4 and at least one pharmaceutically acceptable carrier, diluent, or excipient.

19. A method of treating acute myeloid leukemia, breast or prostate cancer in a mammal comprising administering to the mammal the pharmaceutical composition of claim 18.

20. A method of treating acute myeloid leukemia, breast or prostate cancer in a mammal comprising administering to the mammal the pharmaceutical composition of claim 15.

* * * * *